United States Patent [19]

Berthoux et al.

[11] 3,974,227

[45] Aug. 10, 1976

[54] ACID EXTRACTED-ALKALIZED/CARBON CATALYST SUPPORT WITH COORDINATION COMPLEX CATALYST AND METHOD OF MANUFACTURE

[75] Inventors: Jean Berthoux, Decines; Jacques-Pierre Martinaud, Lyon, both of France

[73] Assignee: Rhone-Progil, Paris, France

[22] Filed: Mar. 20, 1975

[21] Appl. No.: 560,144

Related U.S. Application Data

[63] Continuation of Ser. No. 308,458, Nov. 21, 1972, abandoned.

[30] Foreign Application Priority Data

Dec. 17, 1971  France .............................. 71.46501

[52] U.S. Cl. .......................... 260/604 HF; 252/428; 252/429 R; 252/431 N; 252/431 P; 252/425; 252/444; 252/447
[51] Int. Cl.² ................... C07C 45/10; B01J 31/18; B01J 31/24; B01J 21/18
[58] Field of Search ............ 252/431 P, 431 R, 444, 252/447, 425, 428, 429 R, 431 N; 260/604 HF

[56] References Cited

UNITED STATES PATENTS

| | | | |
|---|---|---|---|
| 1,626,848 | 3/1927 | Liebknecht | 252/425 |
| 2,481,300 | 9/1949 | Engel | 252/447 |
| 3,018,288 | 1/1962 | Tokime | 252/425 |
| 3,487,112 | 12/1969 | Pavlik et al. | 252/431 P |
| 3,499,932 | 3/1970 | Pruett et al. | 252/431 P |
| 3,499,933 | 3/1970 | Pruett et al. | 252/431 P |
| 3,527,809 | 9/1970 | Pruett et al. | 252/431 R |
| 3,576,767 | 4/1971 | Summers | 252/444 |
| 3,733,362 | 5/1973 | Biale | 260/604 HF |
| 3,736,265 | 5/1973 | Suggit | 252/447 |

OTHER PUBLICATIONS

*Journal of Catalysis* 15 (1969), pp. 245–249, "Catalytic Vapor Phase Hydroformylation of Propylene Over Supported Rhodium Complexes" by K. K. Robinson et al.

*Primary Examiner*—Winston A. Douglas
*Assistant Examiner*—P. E. Konopka
*Attorney, Agent, or Firm*—Browdy and Neimark

[57] ABSTRACT

A catalyst for hydrogenation, hydroformylation, olefin oxidation and similar reactions is prepared by treating activated carbon first with a volatile acid and then with a basic substance to provide a suitable support for the catalyst, and then adsorbing onto such support a coordination complex of a transition metal. The adsorption of the catalyst onto the support may be effected in situ during the hydrogenation, hydroformylation, oxidation, etc. reaction.

9 Claims, No Drawings

ACID EXTRACTED-ALKALIZED/CARBON CATALYST SUPPORT WITH COORDINATION COMPLEX CATALYST AND METHOD OF MANUFACTURE

This is a continuation of application Ser. No. 308,458, filed Nov. 21, 1972, now abandoned.

FIELD OF INVENTION

The present invention relates to catalyst supports, catalysts with such supports, and their methods of preparation; and, more particularly, to the preparation of supports of activated carbon for catalysts of coordination, complexes of transition metals.

BACKGROUND OF INVENTION

It is known that coordination complexes of transition metals are very good catalysts for a wide variety of reactions including, particularly, hydrogenation, hydroformylation and olefin oxidation. When these reactions are carried out in the liquid phase, the coordination complexes used as catalysts are almost invariably in a dissolved state in the reaction medium. Inasmuch as the price of the metals used in these coordination complexes is high, it is necessary, from an economic standpoint, to recover such complexes from the reaction medium, since otherwise the cost of the reaction is economically unfeasible. A difficulty exists, however, in the fact that these necessary recovery operations are expensive in themselves. Many recovery operations have been suggested. Thus, the residues of the distillation of the reaction mixture, which contain the catalyst, can be recycled directly to the reaction, but this method is not very satisfactory; in fact, such a simple recycling results in substantial losses and significant poisoning of the catalyst complexes, taking into account the limited stability of such complexes. Other techniques of recovering such complexes have also been suggested, such as separation by osmosis, insolubilization, etc.

Because of the difficulty of the separation procedures as noted above, it has also been suggested that recovery could be avoided if the coordination complexes were adsorbed on solid supports so as to reduce their concentration in the reaction mixture. Classical supports have been suggested for this purpose, but commercialization has not yet been achieved, presumably because of the poor experimental results which have heretofore been obtained by using the classical supports.

In the work leading up to the present invention, applicants studied such classical supports and determined that they are generally unsatisfactory in that they either serve to inhibit the development of the desired reactions to be catalyzed and/or they do not satisfactorily serve to retain the coordination complex catalysts out of solution. Thus, it has been determined that while alumina and silica involve practically no reduction in the yield of the catalyzed reaction, they have a very weak power of retention of the complexes, so that the complexes are found predominantly in the reaction effluent. On the other hand, it has been determined that various activated carbons retain the catalyst in a suitable manner, but serve to practically entirely inhibit the desired reactions.

SUMMARY OF THE INVENTION

It is, accordingly, an object of the present invention to overcome the deficiencies of the prior art, such as indicated above.

It is another object of the present invention to provide for more economical hydrogenation, hydroformylation, olefin oxidation, etc. type reactions.

It is another object of the present invention to obviate the necessity of recovery of coordination complexes of transition metals in reactions such as hydrogenation, hydroformylation, olefin oxidation, etc.

It is another object of the present invention to provide an improved catalytic system.

It is another object of the present invention to provide an effective support for a coordination complex type catalyst, which support permits the catalyst to be entirely effective and yet retains the catalyst out of solution.

It is another object of the present invention to provide a method for the preparation of an effective support for a coordination complex type catalyst.

It is another object of the present invention to provide a method for the preparation of an improved supported catalyst.

These and other objects have now been accomplished by providing catalyst supports having an excellent power of retention and exerting no deleterious effect on the reactions in which the catalysts are to be involved. In use of the supported catalysts of the present invention, it is found that the concentration of coordination complex in the liquid phase is very low, the catalytic reaction apparently occurs in the solid phase, and the recovery of catalysts from the liquid phase effluent is no longer necessary. The supported catalysts can be reused without reactivation for numerous successive operations.

The present invention involves a process for the preparation of supports for catalysts of coordination complexes of transition metals, using activated carbon; this process comprises treating the activated carbon first by contacting it with an aqueous solution of a volatile acid, drying, and then treating the dried carbon with a mineral basic substance. In preparing the supported catalyst, the desired coordination complex is then deposited on the resultant treated activated carbon support.

It has been found that the above-mentioned acidic and basic treatments of the support give the activated carbon the desirable qualities necessary for catalytic supports, which the previous supports have lacked. It is theorized, although the invention is not to be limited to this theory, that the inhibitory effect which untreated activated carbon has on reactions such as hydroformylation of olefins is due to the presence of acid-extractable impurities in the untreated activated carbon, and/or to the presence of free acidic functions; and that, to the contrary, the absence of the inhibition effect and the power to retain the coordination catalysts depends primarily upon a certain range of carbon alkalinity. Thus, it is theorized that the acidic treatment removes non-desirable impurities, and the following treatment with a mineral basic substance restores the desired alkalinity; it is also believed that the acidic treatment makes the following adjustment of alkalinity of the activated carbon easier.

The nature and advantages of the instant invention, as well as other objectives, will be more clear from the following detailed description of certain specific embodiments, it being understood that such embodiments are presented illustratively rather than limitatively.

DETAILED DESCRIPTION OF EMBODIMENTS

As mentioned above, the treated activated carbon support of the present invention, onto which the coordination complex of transition metal is deposited, is provided first by treatment with a volatile acid and then, after drying, by treatment of the carbon with a mineral basic substance. The selection of any particular type of activated carbon is not critical. Thus, any kind of common activated carbon may be used as the starting material, for example products obtained by carbonization of substances, such as sugars, wood particles, etc., and which have undergone an activation operation in accordance with known techniques. Any of such commonly commercially available pre-activated carbons may be subject to the treatment of the present invention and then used as the catalyst support.

The selection of the volatile mineral or organic acid for the first stage treatment of the pre-activated carbon is also not critical. Thus, any volatile mineral or organic acid may be selected, although those which are more readily available and inexpensive are preferred, such as, for example, hydrochloric acid, formic acid, acetic acid, etc. It will also be understood that less volatile acids may also be used if desired, although these less volatile acids tend to complicate the processing in that they require time, temperature and/or vacuum for the drying operation. Based on the present disclosure, those having normal skill in the art will be able to test other acids to determine their processing convenience for purposes of the present invention. However, it is recommended that hydrochloric acid be used because of its low cost and because it is easy to volatilize without the use of substantial energy.

The concentration of the acid in its aqueous solution is not particularly critical, and can vary within a large range; as a rule, however, best results are obtained with solutions containing 0.5 – 20% by weight of acid, and preferably 1 — 10% by weight. The ratio of the pre-activated carbon with regard to the aqueous acid solution in which the carbon is bathed is advantageously selected so that the quantity of acid present is substantially greater than the estimated consumption of the acid. Taking into account the considerable variation in the concentration of the acid, 5 — 20 ml. volume of the aqueous acid solution, more particularly 8 — 15 ml. of the aqueous solution, are used per gram of pre-activated carbon.

The acidic treatment is carried out by keeping the pre-activated carbon in suspension in the aqueous acidic solution, preferably at room or ambient temperature, for a suitable time to ensure that reaction between the impurities and the acid is complete, such as preferably for about 5 to 24 hours. When this operation has been completed, the activated carbon is separated from the liquid and is dried so that all acid and residual moisture are removed. If desired, the drying may be preceded by washing with a fresh charge of the acidic aqueous solution and/or with water.

After drying, the so said treated pre-activated carbon is then treated with a mineral basic substance, preferably an aqueous solution thereof. As a mineral basic substance, there may be used any of the hydroxides of the alkali metals or of the alkaline-earth metals, carbonates of the alkali-metals, or mixtures of such mineral basic substances. As examples there may be mentioned sodium hydroxide, calcium hydroxide, barium hydroxide and sodium carbonate.

According to a first method of carrying out such an alkalizing treatment, a sufficient quantity of this mineral basic substance can be added to the carbon in order to reach the desired degree of alkalinity so as to provide the activated carbon with the desired qualities as expressed above. The quantity required for any operation can be determined ahead of time by means of a simple preliminary test, e.g. a simple trial and error, such as by adding a selected quantity of the mineral basic substance to a sample of the carbon to be treated, testing the retention power of the so-treated sample, and increasing the proportions of the basic mineral substance chosen depending on the results of the first test, and again estimating the retention power and the consequential effects on the reaction of the sample of treated activated carbon. A range of proportions is in this manner defined, which will permit the required results to be obtained.

It is preferred to carry out this preliminary operation to determine the optimum quantity of basic mineral substance to be used since this maximizes the desired results. Thus, in general the treatment with basic mineral substance to provide final activated carbon quality is so controlled as to balance the desired qualities, i.e. to maximize the conversion of reactants during usage while keeping the ratio of retention of the complex on the carbon at an acceptable level, or by maximizing the retention of the complex while keeping the ratio of conversion during usage of the catalyst at an acceptable level.

For example, 2 grams of an activated carbon were treated with increasing quantities of sodium hydroxide and then the resulting effect of these treatments was determined by usage of the supported catalysts in the hydroformylation of hexene, using as the active catalyst the complex $Rh\ Cl\ [P\ (OC_6H_5)_3]_3$ at a concentration of 100 parts per million of the rhodium with regard to the reaction mixture. The reaction conditions were as follows: temperature 100°C.; partial pressure of CO and $H_2$ were 10 bars; acetone was used as a solvent; duration of procedure was 6 hours. The results obtained are shown in Table 1 below:

TABLE 1

| Quantity of added Na hydroxide | | Ratio of transformation of hexene (% in moles) | Rh in the effluent (parts per million) |
|---|---|---|---|
| 0.08 | milliequivalents | 0 | <1 |
| 0.16 | '' | 8 | 1 |
| 0.20 | '' | 80 | 4 |
| 0.26 | '' | 80 | 5 |
| 0.32 | '' | 92 | 7 |
| 0.40 | '' | 99 | 19 |

The results of Table 1 show that, starting with the same activated carbon starting material, a quantity of NaOH of between 0.10 and 0.20 milliequivalents per gram of support can be selected to provide a satisfactory balance between the absence of inhibitory effect during the usage reaction and the retention on the support of sufficient catalyst. The treatment with basic mineral substance is merely carried out by depositing the basic substance on the carbon according to known methods; for example, the acid treated pre-activated carbon may be deposited in an aqueous solution of the desired quantity of basic substance followed by evaporation of water from the aqueous solution.

According to a second method of treating the said treated pre-activated carbon with the basic mineral substance, the treatment is carried out by means of an aqueous and very dilute solution of the basic mineral substance. It has been surprisingly found that, when utilizing such a dilute solution, the desired qualities can be successfully given to any kind of acid-treated, pre-activated carbon, independent of its starting characteristics. By a very dilute solution of the basic mineral substance, what is meant is a concentration of the basic substance in water of between $1 \times 10^{-1}$ and $1 \times 10^{-3}$ moles/liter of solution, preferably $5 \times 10^{-2}$ to $5 \times 10^{-3}$.

As in the case of the acidic treatment, there may be used such a ratio of aqueous solution of basic mineral substance, with regard to the acid treated pre-activated carbon, that the quantity of the basic solution is greatly in excess with regard to the consumption which can be foreseen. In other words, it is advantageous for the alkaline treatment to use such a quantity of solution that the ratio of its final concentration to its starting concentration is close to 1. Generally, it is desirable to use 50 to 100 parts by weight of solution, preferably 60 to 80 parts, per part by weight of carbon. In this operation the acid treated activated carbon is merely suspended in the dilute basic solution at ordinary temperature for an adequate time, preferably for about 5 to 24 hours, to effectuate the desired results; the activated carbon is then removed from the solution and is dried.

The acid and alkaline treated catalyst is then ready for use. It can be used as a support for any known type of coordination complex of a transition metal, such as those containing cobalt, molybdenum, rhodium, platinum and nickel, and ligands such as phosphorus derivatives, carboxylates and so forth. Among these there may be briefly mentioned the catalysts set forth in U.S. Pat. No. 3,527,809, including the prior catalysts discussed in column 1 thereof; the catalysts of U.S. Pat. No. 3,530,190; the catalysts of French Pat. No. 1,459,643; and the prior catalysts discussed in the introductory portions of the applicant's copending application Ser. No. 62,638. However, the present invention is particularly suitable for the complexes described and claimed in applicant's copending application Ser. No. 62,638 of Aug. 10, 1970.

These last mentioned catalyst complexes have the general formula:

$$[M\ Cl_x\ H_y\ (CO)_z\ L_t]$$

wherein

M is the metal nickel, rhodium, palladium, iridium or platinum;

$x + y = 1$ when M is rhodium or iridium;

$x$ and $y = 0$ for the other metals;

the total of $x + y + z + t = 4$; and

L is a ligand selected from the group consisting of aliphatic and aromatic phosphites, aminophosphines, and — where $y = 1$ and $z$ - $0$ — aliphatic and aromatic phosphines.

The complexes can be deposited on the present supports by conventional methods, for example by spraying solutions of the complex in an organic solvent onto the support, followed by evaporation of the solvent. As a matter of fact, the preliminary depositing of the active complexes is not essential, because it is possible to merely introduce the support and the active catalyst into the reaction mixture, in which case the fixation of the complex on the treated activated carbon is carried out in situ before and/or during the usage reaction. In this case, the effluent of the reaction contains no more catalysts than when fixation is achieved beforehand by the conventional methods.

It will be understood that the supported catalysts, i.e. the association of the treated pre-activated carbon and the coordination complex of the transition metal, can be used in any kind of reaction in which such active catalysts have been previously used; for example in hydrogenation, hydroformylation and the oxidation of olefins. The supported catalyst is particularly suitable for hydroformylation which involves, as is known, reacting hydrogen and carbon monoxide with an olefinic compound under pressure and generally in the presence of an organic solvent. With regard to this reaction, it has been determined that the supported catalysts according to the present invention is particularly effective when an aliphatic ketone, such as acetone or methylethyl ketone, is used as the solvent. Because of the support, it has been found that the reaction can be carried out repeatedly with the same supported catalyst, either continuously or batchwise, without appreciably lowering the conversion of the reactants.

In order to better point out the invention and to emphasize the objects of the invention and make the advantages more apparent, the following examples are presented in a non-limitative way:

EXAMPLE 1

Samples of 30 g. of pre-activated carbon with a specific surface of 1100 m²/g and a pH of 5 – 7 were dipped in 400 ml. of an aqueous solution of hydrochloric acid at 1%, and were maintained in suspension in the liquid, by agitating for 24 hours at room temperature (20° – 22°C.). Then the carbon was filtered off, washed first with the same acidic solution, then with water, and dried at 120°C. under a pressure of $10^{-2}$ mm Hg. for 24 hours. Each of these treated samples was then put in suspension in 2 liters of an aqueous solution of a basic substance as set forth in Table 2 below for 24 hours, the treated carbon was then filtered off and dried as in the preceding treatment. The so-treated products were ready for use as supports for the catalyst.

Table 2

| Sample | Basic substance type | Concentration moles/liter |
|---|---|---|
| A | Na OH | $1.10^{-1}$ |
| B | Na OH | $1.10^{-2}$ |
| C | Na OH | $5.10^{-3}$ |
| D | Ca (OH)$_2$ | $2.10^{-2}$ |
| E | Ba (OH)$_2$ | $1.10^{-2}$ |
| F | Na$_2$CO$_3$ | $5.10^{-2}$ |

EXAMPLE 2

In order to prove their effectiveness, supports according to Example 1 were used in a hydroformylation reaction, which was carried out under the following conditions:

Into a reactor fitted with an agitator and a device for injecting gasses, there were introduced, 10 ml. of 1-hexene, 10 ml. of acetone, 3 g. of support, 0.02 g. of Rh Cl[P (O C$_6$H$_5$)$_3$]$_3$ (which corresponds to a calculated concentration of 100 ppm. of rhodium in the liquid effluent, if there is no retention by the support). Then, after blowing the apparatus free of air with carbon monoxide, the liquid was put under partial pressures of 10 bars of hydrogen and 10 bars of carbon monoxide. The mixture was then heated at 100°C. for 6 hours. After cooling and decompressing of the autoclave, the reaction-liquid was centrifuged. Its content in organic reaction products was determined by vapor phase chromatography, and the amount of rhodium contained in the liquid was determined by emission spectrophotometry.

As a comparison the same tests were carried out using the following samples of pre-activated carbon:

Sample:G: treated only with an aqueous solution containing $2 \times 10^{-2}$ mole of Ca $(OH)_2$;

Sample H: treated only with an aqueous solution containing 1% by weight of HCl;

Sample K: treated as in Example 1 (D), but to which the dried extract of the used acidic solution was added;

Sample L: non-treated.

The obtained results are shown in Table 3.

Table 3

| Sample | Conversion ratio of hexene | Amount of rhodium in the reaction liquid (parts/million) |
|---|---|---|
| A | 100 | 70 |
| B | 91 | 4 |
| C | 78 | 2 |
| D | 94 | 5 |
| E | 100 | 28 |
| F | 97 | 35 |
| G | <1 | 1 |
| H | 0 | 1 |
| K | 0 | 1 |
| L | 0 | <1 |

When comparing the supports A to F on the one hand, and G to L on the other hand, it is obvious that the process according to the present invention eliminates inhibitory effect of carbons on the reaction. Moreover, it can be seen that, by varying the molar concentrations of basic substance in the second stage of the process, a satisfactory equilibrium between development of reaction and retention of the complex can be obtained.

Example 3

An activated carbon having a specific area of 1450 m²/g and pH of 9 was treated as in Example 1, successively with an aqueous solution containing 1% of HCl and $1 \times 10^{-2}$ mole of Ca $(OH)_2$/liter. This support was then used in a test identical with the one of Example 2. As a comparison the same test of hydroformylation was made, but with non-treated carbon. The obtained results appear in Table 4.

Table 4

| Carbon | Conversion ratio of hexene (% in moles) | Amount of rhodium in the reaction liquid (parts/million) |
|---|---|---|
| treated | 100 | 5 |
| non-treated | 55 | 19 |

This example shows how advantageous the process according to the invention is to appreciably improve the qualities of carbon as a support both in the reduction of inhibition effect on the reaction and in the retention of the complex, when the starting carbon itself has those characteristics to a much smaller degree.

EXAMPLE 4

A series of tests of hydroformylation were conducted by starting with 10 ml. 1-hexene and 10 ml. of acetone and were carried on as in the previous examples. The same catalytic association i.e. the one obtained from support D, such as it was recovered at the end of the test of Example 2, was used every time. In addition, 1.5 mg. of triphenylphosphite was added in each test. The obtained results are shown in Table 5.

Table 5

| no. of the test | Conversion ratio of hexene (% in moles) |
|---|---|
| Example 2 (remainder) | 94 |
| 4 - 1 | 91 |
| 4 - 2 | 89 |
| 4 - 3 | 86 |
| 4 - 4 | 93 |
| 4 - 5 | 87 |

As it can be seen, the catalytic association according to the invention is not appreciably deactivated during these successive operations.

It is to be understood that the invention is not limited to the embodiments disclosed above which are offered illustratively, and that modifications may be made without departing from the invention.

What is claimed is:

1. A process for the preparation of a supported catalyst of a coordination complex of a transition metal useful in liquid phase reactions of olefin hydrogenation, hydroformylation and oxidation, of pre-activated carbon comprising:

contacting said pre-activated carbon with an amount of aqueous solution of a volatile acid sufficient to substantially eliminate by reaction therewith the acid-extractable impurities in said carbon, said aqueous solution of volatile acid comprising 0.5 to 20% by weight of said acid and being present in a large excess — compared with the quantity theoretically needed to eliminate the acid-extractable impurities — during its contact with said pre-activated carbon;

drying said acid treated pre-activated carbon;

treating said dried, acid treated, pre-activated carbon to render the carbon alkaline with an aqueous solution of a mineral basic substance containing $1 \times 10^{-1}$ to $1 \times 10^{-3}$ moles of said mineral basic substance from the group consisting of alkali and alkaline-earth hydroxides and alkali carbonates per liter of solution, said aqueous solution of mineral basic substance being present in a large excess — such that the ratio of its final concentration to its starting concentration is approximately one — during the contact with said dried, acid treated, pre-activated carbon;

drying the so base-treated carbon; and depositing said coordination complex on the so-treated carbon in liquid phase, wherein said coordination complex has the formula [M $Cl_x$ $H_y$ $(CO)_z$ $L_t$]

wherein

M is the metal nickel, rhodium, palladium, iridium or platinum;

$x + y = 1$ when M is rhodium or iridium;

$x$ and $y = 0$ for the other metals;

the total of $x + y + z + t = 4$; and

L is a ligand selected from the group consisting of aliphatic and aromatic phosphites, aminophosphines, and — where $y = 1$ and $z = 0$ — aliphatic and aromatic phosphines.

2. A process in accordance with claim 1 wherein said volatile acid is hydrochloric acid.

3. A process according to claim 1 wherein said aqueous solution of volatile acid is present in an amount of 5 – 20 ml. per gm. of carbon.

4. A process in accordance with claim 1 wherein said mineral basic substance is sodium hydroxide, calcium hydroxide, barium hhydroxide, or sodium carbonate.

5. A process in accordance with claim 1 wherein said aqueous solution of acid contains 1 to 10% by weight of acid, and said basic mineral substance comprises an aqueous solution of said mineral substance containing $5 \times 10^{-2}$ to $5 \times 10^{-3}$ moles of said basic substance per liter of solution.

6. A supported catalyst comprising a product obtained by the process of claim 1.

7. A process in accordance with claim 1 for preparing a supported catalyst wherein said depositing of said coordination complex on said carbon comprises:
   mixing, in reactor, an olefin, hydrogen, carbon monoxide, a solvent comprising an aliphatic ketone, said coordination complex of a transition metal, and said carbon; and
   carrying out a hydroformylation reaction and simultaneously fixing the active catalyst on the activated carbon support.

8. A process in accordance with claim 1 for the preparation of a supported catalyst of a coordination complex of a transition metal useful in liquid phase reactions of olefin hydrogenation, hydroformylation and oxydation, from pre-activated carbon, comprising:
   contacting said pre-activated carbon with 5 – 20 ml of an aqueous 0.5 – 20% solution of a volatile acid per gram of pre-activated carbon, at room temperature for 5 – 24 hours, said volatile acid being selected from the group consisting of hydrochloric acid, formic acid and acetic acid;
   drying said acid-treated pre-activated carbon;
   contacting said dried, acid-treated, pre-activated carbon with 50 – 100 parts by weight, per part by weight of said carbon, of an aqueous solution containing $1 \times 10^{-1}$ to $1 \times 10^{-3}$ mols per liter of a mineral basic substance selected from the group consisting of sodium hydroxide, calcium hydroxide, barium hydroxide and sodium carbonate, for 5 – 24 hours;
   and drying said carbon.

9. A process in accordance with claim 1 wherein the step of depositing said coordination complex on the acid and base-treated pre-activated carbon in liquid phase comprises:
   mixing said complex and said so-treated pre-activated carbon in a solvent in which adsorption can take place.

* * * * *